(12) United States Patent
Benco

(10) Patent No.: US 7,927,620 B2
(45) Date of Patent: Apr. 19, 2011

(54) MEDICAL DEVICES HAVING ANTIFOULING CHARACTER

(75) Inventor: John Benco, Holliston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 381 days.

(21) Appl. No.: 11/803,499

(22) Filed: May 15, 2007

(65) Prior Publication Data

US 2008/0286326 A1 Nov. 20, 2008

(51) Int. Cl.
*A61F 2/82* (2006.01)
*B32B 27/28* (2006.01)
*C08G 65/40* (2006.01)
*C08G 73/10* (2006.01)

(52) U.S. Cl. .................. 424/423; 428/473.5; 528/170; 528/219; 528/271; 528/322; 528/363; 528/392; 528/425

(58) Field of Classification Search .................. None
See application file for complete search history.

(56) References Cited

U.S. PATENT DOCUMENTS

| 2003/0087338 | A1 | 5/2003 | Messersmith et al. | 435/68.1 |
| 2005/0208093 | A1* | 9/2005 | Glauser et al. | 424/423 |
| 2005/0245637 | A1* | 11/2005 | Hossainy et al. | 523/113 |
| 2005/0266038 | A1 | 12/2005 | Glauser et al. | |
| 2006/0009550 | A1 | 1/2006 | Messersmith et al. | 524/17 |
| 2008/0286333 | A1 | 11/2008 | Kangas | |

FOREIGN PATENT DOCUMENTS

WO WO 2006/055531 A2 5/2006

OTHER PUBLICATIONS

Statz et al. "New Peptidomimetic Polmers for Antifouling Surfaces" J. Am. Chem. Soc. 2005, 127, 7972-7973.*
M. Zhang et al. "Proteins and cells on PEG immobilized silicon surfaces", *Biomaterials*, 19, 1998, p. 953-960.
D.W. Branch et al., "Long-term stability of grafted polyethylene glycol surfaces for use with microstamped substrates in neuronal cell culture", *Biomaterials*, 22, 2001, pp. 1035-1047.
Y. Zhang et al., "Study of protein absorption on polymer coatings surface by combining quartz crystal microbalance with electrochemical impedance methods", *Sensors and Actuators B*, 108, 2005, pp. 933-942.
E. Ostuni et al., "A Survey of Structure-Property Relationships of Surfaces that Resist the Adsorption of Protein", *Langmuir*, 2001, 17, pp. 5605-5620.
A.R. Statz et al., "New Peptidomimetic Polymers for Antifouling Surfaces", *J. Am. Chem. Soc.*, 2005, 127, pp. 7972-7973.
T. Horn et al., "Incorporation of Chemoselective Functionalities into Peptoids via Solid-Phase Submonomer Synthesis", *Bioconjug. Chem.*, 15, 2004, pp. 428-435.
J. Rennie et al., "Simple oligomers as antimicrobial peptide mimics", *J. Ind. Microbiol. Biotechnol*, 2005, 32, pp. 296-300.
J. L. Dalsin et al., "Bioinspired antifouling polymers", *Materials Today*, Sep. 2005, pp. 38-46.
Lee Ayres, "From structural proteins to synthetic polymers", Doctoral Thesis, Radboud Universiteit Nijmegen, 2005, ISBN 9090198075, Chapter 1.
Lee Ayres et al., "Peptide-Polymer Vesicles Prepared by Atom Transfer Radical Polymerization" *Journal of Polymer Science Part A: Polymer Chemistry*, vol. 43, Issue 24, 2005, pp. 6355-6366.
Mattijs G.J. Ten Cate et al., "Sequence-Defined Polypeptide-Polymer Conjugates Utilizing Reversible Addition Fragmentation Transfer Radical Polymerization", *Macromolecules*, 2005, vol. 38, No. 26, pp. 10643-10649.
Pyun et al., "Synthesis of Nanocomposite Organic/Inorganic Hybrid Materials Using Controlled/"Living" Radical Polymerization," *Chem. Mater.*, 13, 2001, pp. 3436-3448.
B. Reeves, "Recent Advances in Living Free Radical Polymerization," Nov. 20, 2001, University of Florida, 14 pages.
T. Kowalewski et al., "Complex nanostructured materials from segmented copolymers prepared by ATRP," *Eur. Phys. J. E*, 10, 2003, pp. 5-16.
N. V. Tsarevsky et al., "Step-Growth "Click" Coupling of Telechelic Polymers Prepared by Atom Transfer Radical Polymerization", *Macromolecules*, 2005, 38, 3558.
Glenn Westwood et al., "Simplified Polymer Mimics of Cross-Linking Adhesive Proteins", Macromolecules, 2007, 40, 3960-3964.

* cited by examiner

*Primary Examiner* — Robert A Wax
*Assistant Examiner* — Danah Al-Awadi
(74) *Attorney, Agent, or Firm* — Mayer & Williams PC; David B. Bonham; Keum J. Park

(57) ABSTRACT

According to an aspect of the invention, medical devices are provided which include (a) a substrate and (b) a coating that includes an antifouling copolymer, an adhesive copolymer, or both. Antifouling copolymers for use in conjunction with the present invention contain (i) at least one antifouling polymer block having multiple pendant alkoxy functional groups along the polymer backbone and (ii) at least one additional polymer block. Adhesive copolymers for use in conjunction with the present invention contain (i) at least one adhesive polymer block having multiple pendant ring-hydroxyl-substituted aromatic groups along the polymer backbone and (ii) at least one additional polymer block.

42 Claims, 1 Drawing Sheet

MEDICAL DEVICES HAVING ANTIFOULING CHARACTER

FIELD OF THE INVENTION

The present invention relates generally to medical devices, and more particularly to implantable or insertable medical devices.

BACKGROUND OF THE INVENTION

Significant effort has been placed into the development of medical devices which are resistant to protein, cell and bacterial fouling. Prime examples are vascular stents in which protein fouling has been implicated in thrombosis. Such stents have become the standard of care for maintaining vessel patency after balloon angioplasty. Typically, these devices are modified with a polymer coating to reduce protein fouling. For example, polymers with polyethylene glycol (PEG) or polyethylene oxide (PEO) have been used to reduce protein fouling but these coatings have met limited success. See, e.g., M. Zhang et al. *Biomaterials,* 1998, 19, 953 and D. W. Branch et al. *Biomaterials,* 2001, 22, 1035. In many cases this is due to poor adhesion or integrity, which results in the loss of protein resistance. To overcome these effects, several strategies have been used to enhance adhesion and film integrity, including, for example, silane tie-layers or mechanical modification of the device surface, but these strategies have yielded questionable results. Moreover, these strategies require several, often difficult or expensive, manufacturing steps to produce the device. In light of these issues, a new and robust technology is desired.

SUMMARY OF THE INVENTION

According to an aspect of the invention, medical devices are provided which include (a) a substrate and (b) a coating that includes an antifouling copolymer, an adhesive copolymer, or both. Antifouling copolymers for use in conjunction with the present invention contain (i) at least one antifouling polymer block having multiple alkoxy functional groups along the polymer backbone and (ii) at least one additional polymer block. Adhesive copolymers for use in conjunction with the present invention contain (i) at least one adhesive polymer block having multiple ring-hydroxyl-substituted aromatic groups along the polymer backbone and (ii) at least one additional polymer block.

An advantage of the present invention is that medical devices may be provided with polymeric coatings which have reduced protein fouling.

Another advantage of the present invention is that medical devices may be provided with polymeric coatings which have improved adhesion to underlying substrates.

These and many other aspects, embodiments and advantages of the present invention will become immediately apparent to those of ordinary skill in the art upon review of the Detailed Description and Claims to follow.

DETAILED DESCRIPTION OF THE INVENTION

Figure 1:
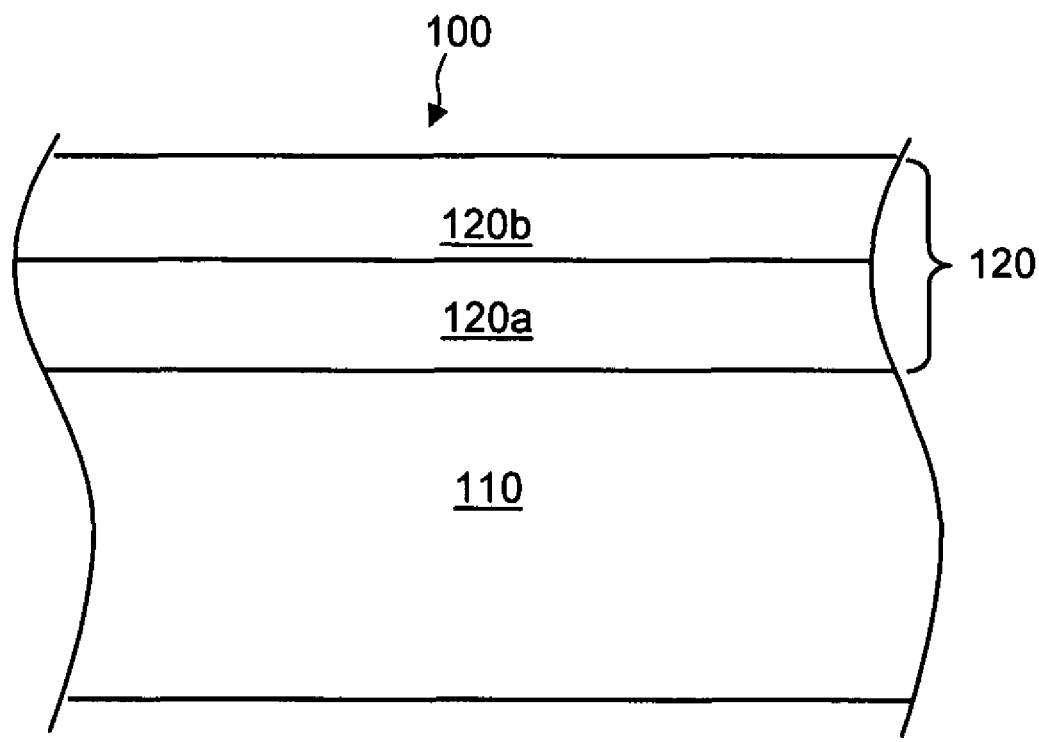
FIG. 1 is a schematic, partial cross-sectional view of a medical device, in accordance with an aspect of the invention.

A more complete understanding of the present invention is available by reference to the following detailed description of numerous aspects and embodiments of the invention. The detailed description of the invention which follows is intended to illustrate but not limit the invention.

As used herein, an "antifouling copolymer" is a copolymer that, when included in a polymeric layer at a medical device surface, reduces protein fouling relative to the fouling which would otherwise occur in the absence of the antifouling copolymer.

As used herein, an "adhesive copolymer" is (a) a copolymer that, when included in a polymeric layer with one or more other polymers, provides improved adhesion of the polymeric layer to an adjacent substrate, relative to such adhesion when the adhesion promoting polymer is not included in the polymeric layer or (b) a copolymer that, when disposed in a first polymeric layer between a substrate and a second polymeric layer, provides improved adhesion of the second polymeric layer to the substrate, relative to such adhesion in the absence of the first polymeric layer.

As used herein a "layer" of a given material is a region of that material whose thickness is small compared to both its length and width. Layers in accordance with the present invention can cover all or only a portion of the underlying metallic substrate, depending on the application. Layers can be provided over an underlying substrate at a variety of locations and in a variety of shapes (e.g., in the form of a series of rectangles, stripes, or any other continuous or non-continuous pattern). As used herein a layer need not be planar, for example, taking on the contours of an underlying substrate.

Adhesion may be evaluated, for example, by so called tape tests (ASTM D-3359) or scrape tests (ASTM D-2197).

Fouling may be evaluated, for example, by use of a quartz crystal microbalance to measure protein adsorption. See, e.g., Y. Zhang et al., *Sensors and Actuators B* 108 (2005) 933-942.

As used herein a "metallic substrate" is one containing metals, for example, from 50 wt % or less to 75 wt % to 90 wt % to 95 wt % to 97.5 wt % to 99 wt % or more metals. These include pure (excluding impurities, native and non-native oxides, etc.) metallic substrates such as those formed from pure metals (e.g. Ti, Ta), and pure metal alloys comprising iron and chromium (e.g., stainless steels, including platinum-enriched radiopaque stainless steel), alloys comprising nickel and titanium (e.g., Nitinol), niobium alloys, titanium alloys, alloys comprising cobalt and chromium, including alloys that comprise cobalt, chromium and iron (e.g., elgiloy alloys), alloys comprising nickel, cobalt and chromium (e.g., MP 35N) and alloys comprising cobalt, chromium, tungsten and nickel (e.g., L605), alloys comprising nickel and chromium (e.g., inconel alloys), among others.

As used herein a "metal oxide substrate" is one containing metal oxides, for example, from 50 wt % or less to 75 wt % to 90 wt % to 95 wt % to 97.5 wt % to 99 wt % or more metal oxides. These include non-transition-metal oxides (e.g., oxides of metals from groups 13, 14 and 15 of the periodic table, including, for example, aluminum oxide) and transition-metal oxides (e.g., oxides of metals from groups 3, 4, 5, 6, 7, 8, 9, 10, 11 and 12 of the periodic table, including, for example, oxides of zirconium, titanium, hafnium, tantalum, molybdenum, tungsten, rhenium, iridium, and so forth), among others.

As used herein, a "polymeric layer" is a layer that contains polymers, for example, from 50 wt % or less to 75 wt % to 90 wt % to 95 wt % to 97.5 wt % to 99 wt % or more polymers.

As used herein, "polymers" are molecules containing multiple copies (e.g., from 2 to 5 to 10 to 25 to 50 to 100 to 250 to 500 to 1000 or more copies) of one or more constitutional units, commonly referred to as monomers. As used herein, the term "monomers" may refer to the free monomers and those that are incorporated into polymers, with the distinction being clear from the context in which the term is used.

Polymers, including the antifouling and adhesive copolymers described herein, may take on a number of configurations, which may be selected, for example, from cyclic, linear and branched configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more polymer blocks that differ in composition, for instance, because a constitutional unit (i.e., a monomer) is found in one polymer block that is not found in another polymer block. As used herein, a "polymer block" or "block" is a grouping of constitutional units (e.g., 5 to 10 to 25 to 50 to 100 to 250 to 500 to 1000 or more units). Blocks can be unbranched or branched. Blocks can contain a single type of constitutional unit (also referred to herein as "homopolymeric blocks") or multiple types of constitutional units (also referred to herein as "copolymeric blocks") which may be present, for example, in a random, statistical, gradient, or periodic (e.g., alternating) distribution.

As used herein, a "chain" is a linear polymer or a portion thereof, for example, a linear polymer block.

Medical devices in accordance with the invention vary widely. Examples include implantable or insertable medical devices, for example, stents (including coronary vascular stents, peripheral vascular stents, cerebral, urethral, ureteral, biliary, tracheal, gastrointestinal and esophageal stents), stent coverings, stent grafts, vascular grafts, catheters (e.g., renal or vascular catheters such as balloon catheters and various central venous catheters), guide wires, balloons, filters (e.g., vena cava filters and mesh filters for distil protection devices), abdominal aortic aneurysm (AAA) devices (e.g., AAA stents, AAA grafts, etc.), vascular access ports, dialysis ports, embolization devices including cerebral aneurysm filler coils (including Guglilmi detachable coils and metal coils), septal defect closure devices, myocardial plugs, patches, pacemakers, lead coatings including coatings for pacemaker leads, defibrillation leads and coils, ventricular assist devices including left ventricular assist hearts and pumps, total artificial hearts, shunts, valves including heart valves and vascular valves, anastomosis clips and rings, cochlear implants, as well as any other coated substrate (which may be, for example, metallic, metal oxide, or polymeric in nature) that is implanted or inserted into the body.

Subjects are vertebrate subjects, more typically mammalian subjects including human subjects, pets and livestock.

According to an aspect of the invention, medical devices are provided which include (a) a substrate and (b) a coating that includes an antifouling copolymer, an adhesive copolymer, or both.

Antifouling copolymers for use in conjunction with the present invention contain (i) at least one antifouling polymer block having multiple alkoxy functional groups along the polymer backbone and (ii) at least one additional polymer block. Examples of alkoxy functional groups include $C_1$-$C_5$-alkoxy groups. Further examples of alkoxy functional groups include alkoxyalkyl groups, for example, $C_1$-$C_5$-alkoxy-$C_1$-$C_5$-alkyl groups, including methoxymethyl groups, methoxyethyl groups, ethoxyethyl groups, methoxypropyl groups, and so forth.

In some embodiments, the alkoxy groups are disposed along an antifouling polymer block that comprises a polyamide backbone, for example, the antifouling polymer block may comprise a poly(amino acid) chain or a peptoid chain. A "peptoid" is a poly(N-substituted amide). The peptoid chain may be, for instance, of the following formula

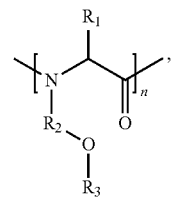

where n is an integer which provides a block length that is sufficient to impart an antifouling character to the antifouling copolymer, $R_1$ and $R_2$ are organic radicals, for example, independently selected from H, $C_1$-$C_6$ alkyl, $C_1$-$C_6$ alkene or $C_6$-$C_{10}$ aromatic, or selected from $C_1$-$C_6$ alkyl, $C_1$-$C_6$ alkene or $C_6$-$C_{10}$ aromatic in combination with one or more heteroatoms such as N, O, or S, and $R_3$ is $C_1$-$C_6$ alkyl. In a specific embodiment, $R_1$ is hydrogen, and $R_2$ and $R_3$ are $C_1$-$C_6$ alkyl, in which case the chain is a poly(N-alkoxyalkyl glycine) chain. In a specific embodiment, n is between 10 and 40, more typically between 15 and 25, more typically about 20, and $R_1$ is hydrogen, $R_2$ is —$CH_2$—$CH_2$— and $R_3$ is —$CH_3$, in which case the chain is a poly(N-methoxyethyl glycine) chain. As a further variation the peptoid block may be of L or D chiral configuration or a combination thereof.

For effective general protein resistance, the residue should be designed based on general principles as suggested by others. See, e.g., E. Ostuni et al., *Langmuir,* 2001, 17, 5605-5620. In particular the segment should possess one or more of the following characteristics: (a) the segment should not contain hydrogen bond donors but should contain hydrogen bond acceptors, (b) the segment should be of neutral charge, and (c) the segment should possess some degree of water compatibility (hydrophilicity).

Peptoid synthesis is commonly based on a "submonomer" approach, which involves (1) acylation of an amino terminated resin bound species with bromoacetic acid (condensation), followed by (2) nucleophilic substitution of the Br group with an amine. This process is repeated until a peptoid of the desired length is synthesized. Solid phase chemistry is typically used because it allows control over the peptide sequence. Further information may be found, for example, in A. R. Statz et al. *J. Am. Chem. Soc.* 2005, 127, 7972-7973, T. Horn et al., *Bioconjug. Chem.* 15: 428-435 (2004), and the references disclosed therein.

Adhesive copolymers for use in conjunction with the present invention contain (i) at least one adhesive polymer block having multiple ring-hydroxyl-substituted aromatic groups along the polymer backbone and (ii) at least one additional polymer block. The ring-hydroxyl-substituted aromatic groups may be, for example, ring-hydroxyl-substituted $C_6$-$C_{12}$-aromatic groups, including hydroxyphenyl groups and dihydroxyphenyl groups, among others. More specific examples include 3-4-dihydroxyphenyl groups and 3,4-dihydroxyphenylalkyl groups, for example, 3,4-dihydroxyphenyl-$C_1$-$C_6$-alkyl groups such as 3,4 dihydroxybenzyl groups, among others.

In some embodiments, the adhesive polymer block further comprises multiple amino-alkyl groups, for example, amino-$C_1$-$C_{10}$-alkyl groups, along the polymer backbone, in addition to the ring-hydroxyl-substituted aromatic groups. More specific examples include amino-$C_2$-$C_6$-alkyl groups (e.g., 2-amino-ethyl groups, 3-amino-n-propyl groups, 4-amino-n-butyl groups, etc.) In certain embodiments, the ring-hydroxyl-substituted aromatic groups and amino-alkyl groups alternate along the length of the polymer backbone.

In some embodiments, the ring-hydroxyl-substituted aromatic groups are disposed along an adhesive polymer block that comprises a polyamide backbone, for example, the adhesive polymer block may comprise a poly(amino acid) chain or a peptoid chain. In a more specific example, the adhesive polymer block comprises a poly(amino acid) chain that comprises multiple (3,4 dihydroxyphenyl alanine) (DOPA) units, which chain may further comprise lysine units adjacent to the DOPA units, for example, in an alternating arrangement. The chain may or may not contain further amino acids other than DOPA and lysine. As a further variation the peptoid block may be of L or D chiral configuration or a combination thereof.

Peptides are generally made by the "Fmoc" synthesis technique in which the carboxyl group of an N-protected amino acid is activated and reacted with the terminal primary amino group of a resin-bound amino acid/peptide, resulting in amide bond formation. Solid phase chemistry is typically used because it allows control over the peptide sequence. For further information, see, e.g., Lee Ayres, *From structural proteins to synthetic polymers*, Doctoral Thesis, Radboud Universiteit Nijmegen, 2005, ISBN 9090198075, Chapter 1 and the references cited therein.

As noted above, antifouling copolymers for use in conjunction with the present invention contain one or more polymer blocks, in addition to at least one antifouling polymer block. Similarly, adhesive copolymers for use in conjunction with the present invention contain one or more polymer blocks in addition to at least one adhesive polymer block.

The one or more additional polymer blocks may vary widely and include biostable polymer blocks, biodegradable polymer blocks, and combinations thereof. The one or more additional polymer blocks may be selected, for example, from the following, among many others: polycarboxylic acid homopolymer and copolymer blocks including polyacrylic acid blocks, polymethacrylic acid blocks, ethylene-methacrylic acid copolymer blocks and ethylene-acrylic acid copolymer blocks, where some of the acid groups can be neutralized; acrylate and methacrylate homopolymer and copolymer blocks (e.g., n-butyl methacrylate blocks); cellulosic homopolymer and copolymer blocks, including cellulose acetates and cellulose ethers such as carboxymethyl celluloses and hydroxyalkyl celluloses; polyoxymethylene homopolymer and copolymer blocks; polyimide homopolymer and copolymer blocks such as polyether block imides, polyamidimide blocks, polyesterimide blocks, and polyetherimide blocks; polysulfone homopolymer and copolymer blocks including polyarylsulfones and polyethersulfones; polyamide homopolymer and copolymer blocks including nylon 6,6, nylon 12, polycaprolactams, polyacrylamides and polyether block amides; polycarbonate blocks; polyacrylonitrile blocks; polyvinylpyrrolidone blocks; homopolymer and copolymer blocks of vinyl monomers including polyvinyl alcohols, polyvinyl halides such as polyvinyl chlorides, ethylene-vinyl acetate copolymer blocks (EVA), polyvinylidene chloride blocks, polyvinyl ether blocks such as polyvinyl methyl ethers, polystyrene blocks, styrene-maleic anhydride copolymer blocks, vinyl-aromatic-alkylene copolymer blocks, including styrene-butadiene copolymer blocks, styrene-ethylene-butylene copolymer blocks, styrene-isoprene copolymer blocks, acrylonitrile-styrene copolymer blocks, acrylonitrile-butadiene-styrene copolymer blocks, styrene-butadiene copolymer blocks and styrene-isobutylene copolymer blocks; polyphosphonate homopolymer and copolymer blocks; polysulfonate homopolymer and copolymer blocks, for example, sulfonated vinyl aromatic homopolymer and copolymer blocks; polyvinyl ketone blocks, polyvinylcarbazole blocks, and polyvinyl ester blocks such as polyvinyl acetates; polybenzimidazole blocks; polyalkyl oxide homopolymer and copolymer blocks including polyethylene oxide blocks; polyester homopolymer and copolymer blocks including polyethylene terephthalates and aliphatic polyesters such as homopolymer and copolymer blocks of lactide (which includes lacetic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one; polyether homopolymer and copolymer blocks including polyarylethers such as polyphenylene ethers, polyether ketones, polyether ether ketones; polyphenylene sulfide blocks; polyisocyanate blocks; polyolefin homopolymer and copolymer blocks, including polyalkylenes such as polypropylenes, polyethylenes, polybutylenes (such as polybut-1-ene and polyisobutylene), poly-4-methyl-pen-1-enes, ethylene-alpha-olefin copolymer blocks, ethylene-methyl methacrylate copolymer blocks and ethylene-vinyl acetate copolymer blocks; fluorinated homopolymer and copolymer blocks, including polytetrafluoroethylene (PTFE), poly(tetrafluoroethylene-co-hexafluoropropene) (FEP), ethylene-tetrafluoroethylene copolymer (ETFE), and polyvinylidene fluoride (PVDF) blocks; silicone homopolymer and copolymer blocks; polyurethane blocks; p-xylylene polymer blocks; polyiminocarbonate blocks; copoly(ether-ester) blocks such as poly(ethylene oxide-lacetic acid) copolymer blocks; polyphosphazine blocks; polyalkylene oxalate blocks; polyoxaamide and polyoxaester blocks; polyorthoester blocks; polyamine and polyimine homopolymer and copolymer blocks; biopolymer blocks, for example, polypeptide blocks, polysaccharide blocks, and glycosaminoglycan blocks.

Examples of biodegradable polymer blocks for use in the present invention, not necessarily exclusive of those listed above, may be selected from suitable members of the following, among many others: (a) polyester homopolymer and copolymer blocks such as polyglycolide (PGA), poly-lactide (PLA) including poly-L-lactide, poly-D-lactide, and poly-D, L-lactide, poly(beta-hydroxybutyrate), poly-D-gluconate, poly-L-gluconate, poly-D,L-gluconate, poly(epsilon-caprolactone), poly(delta-valerolactone), poly(p-dioxanone), poly (trimethylene carbonate), poly(lactide-co-glycolide) (PLGA), poly(lactide-co-delta-valerolactone), poly(lactide-co-epsilon-caprolactone), poly(lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxyphenoxy)propane-co-sebacic acid], and poly(sebacic acid-co-fumaric acid) blocks, among others, (b) poly(ortho ester) blocks such as those synthesized by copolymerization of various diketene acetals and diols, among others, (c) polyanhydride blocks such as poly(adipic anhydride), poly(suberic anhydride), poly(sebacic anhydride), poly(dodecanedioic anhydride), poly(maleic anhydride), poly[1,3-bis(p-carboxyphenoxy)

methane anhydride], and poly[alpha,omega-bis(p-carboxyphenoxy)alkane anhydride] blocks such as poly[1,3-bis(p-carboxyphenoxy)propane anhydride] and poly[1,3-bis(p-carboxyphenoxy)hexane anhydride] blocks, among others; and (d) amino-acid-based polymer blocks including tyrosine-based polyarylate blocks (e.g., copolymer blocks of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonate blocks (e.g., copolymer blocks formed by the condensation polymerization of phosgene and a diphenol selected, for instance, from ethyl, butyl, hexyl, octyl and bezyl esters of desaminotyrosyl-tyrosine), and tyrosine-, leucine- and lysine-based polyesteramide blocks; specific examples of tyrosine-based polymers include includes polymer blocks that are comprised of a combination of desaminotyrosyl tyrosine hexyl ester, desaminotyrosyl tyrosine, and various di-acids, for example, succinic acid and adipic acid.

In some embodiments, the one or more additional polymer blocks may be selected based on glass transition temperature. For example, a "soft polymer block," also referred to as a "low Tg polymer block," is one that displays a Tg that is below body temperature, more typically from 35° C. to 20° C. to 0° C. to −25° C. to −50° C. or below. A low Tg monomer is one that displays a Tg that is below body temperature when formed into a homopolymer. Conversely, as used herein, a "hard polymer block," also referred to as a "high Tg polymer block," is one that displays a Tg that is above body temperature, more typically from 40° C. to 50° C. to 75° C. to 100° C. or above. A high Tg monomer is one that displays a Tg that is above body temperature when formed into a homopolymer. Tg can be measured by differential scanning calorimetry (DSC).

Specific examples of low Tg polymer blocks include homopolymer and copolymer blocks containing one or more of the following low Tg monomers (listed along with published Tg's for homopolymers of the same): (1) unsubstituted and substituted alkene monomers including ethylene, propylene (Tg −8 to −13° C.), isobutylene (Tg −73° C.), 1-butene (Tg −24° C.), 4-methyl pentene (Tg 29° C.), 1-octene (Tg −63° C.) and other α-olefins, dienes such as 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, and 3-butyl-1,3-octadiene, and halogenated alkene monomers including vinylidene chloride (Tg −18° C.), vinylidene fluoride (Tg −40° C.), cis-chlorobutadiene (Tg −20° C.), and trans-chlorobutadiene (Tg −40° C.); (2) acrylic monomers including: (a) alkyl acrylates such as methyl acrylate (Tg 10° C.), ethyl acrylate (Tg −24° C.), propyl acrylate, isopropyl acrylate (Tg −11° C., isotacetic), n-butyl acrylate (Tg −54° C.), sec-butyl acrylate (Tg −26° C.), isobutyl acrylate (Tg −24° C.), cyclohexyl acrylate (Tg 19° C.), 2-ethylhexyl acrylate (Tg −50° C.), dodecyl acrylate (Tg −3° C.) and hexadecyl acrylate (Tg 35° C.), (b) arylalkyl acrylates such as benzyl acrylate (Tg 6° C.), (c) alkoxyalkyl acrylates such as 2-ethoxyethyl acrylate (Tg −50° C.) and 2-methoxyethyl acrylate (Tg −50° C.), (d) halo-alkyl acrylates such as 2,2,2-trifluoroethyl acrylate (Tg −10° C.) and (e) cyano-alkyl acrylates such as 2-cyanoethyl acrylate (Tg 4° C.); (3) methacrylic monomers including (a) alkyl methacrylates such as butyl methacrylate (Tg 20° C.), hexyl methacrylate (Tg −5° C.), 2-ethylhexyl methacrylate (Tg −10° C.), octyl methacrylate (Tg −20° C.), dodecyl methacrylate (Tg −65° C.), hexadecyl methacrylate (Tg 15° C.) and octadecyl methacrylate (Tg −100° C.) and (b) aminoalkyl methacrylates such as diethylaminoethyl methacrylate (Tg 20° C.) and 2-tert-butyl-aminoethyl methacrylate (Tg 33° C.); (4) vinyl ether monomers including (a) alkyl vinyl ethers such as methyl vinyl ether (Tg −31° C.), ethyl vinyl ether (Tg −43° C.), propyl vinyl ether (Tg −49° C.), butyl vinyl ether (Tg −55° C.), isobutyl vinyl ether (Tg −19° C.), 2-ethylhexyl vinyl ether (Tg −66° C.) and dodecyl vinyl ether (Tg −62° C.); (5) cyclic ether monomers include tetrahydrofuran (Tg −84° C.), trimethylene oxide (Tg −78° C.), ethylene oxide (Tg −66° C.), propylene oxide (Tg −75° C.), methyl glycidyl ether (Tg −62° C.), butyl glycidyl ether (Tg −79° C.), allyl glycidyl ether (Tg −78° C.), epibromohydrin (Tg −14° C.), epichlorohydrin (Tg −22° C.), 1,2-epoxybutane (Tg −70° C.), 1,2-epoxyoctane (Tg −67° C.) and 1,2-epoxydecane (Tg −70° C.); (6) ester monomers (other than the above acrylates and methacrylates) including ethylene malonate (Tg −29° C.), vinyl acetate (Tg 30° C.), and vinyl propionate (Tg 10° C.); and (7) siloxane monomers including dimethylsiloxane (Tg −127° C.), diethylsiloxane, methylethylsiloxane, methylphenylsiloxane (Tg −86° C.), and diphenylsiloxane.

Specific examples of high Tg polymer blocks include homopolymer and copolymer blocks containing one or more of the following high Tg monomers: (1) vinyl aromatic monomers including (a) unsubstituted vinyl aromatics, such as styrene (Tg 100° C.) and 2-vinyl naphthalene (Tg 151° C.), (b) vinyl substituted aromatics such as alpha-methyl styrene, and (c) ring-substituted vinyl aromatics including ring-alkylated vinyl aromatics such as 3-methylstyrene (Tg 97° C.), 4-methylstyrene (Tg 97° C.), 2,4-dimethylstyrene (Tg 112° C.), 2,5-dimethylstyrene (Tg 143° C.), 3,5-dimethylstyrene (Tg 104° C.), 2,4,6-trimethylstyrene (Tg 162° C.), and 4-tert-butylstyrene (Tg 127° C.), ring-alkoxylated vinyl aromatics, such as 4-methoxystyrene (Tg 113° C.) and 4-ethoxystyrene (Tg 86° C.), ring-halogenated vinyl aromatics such as 2-chlorostyrene (Tg 119° C.), 3-chlorostyrene (Tg 90° C.), 4-chlorostyrene (Tg 110° C.), 2,6-dichlorostyrene (Tg 167° C.), 4-bromostyrene (Tg 118° C.) and 4-fluorostyrene (Tg 95° C.), ring-ester-substituted vinyl aromatics such as 4-acetoxystyrene (Tg 116° C.), ring-hydroxylated vinyl aromatics such as 4-hydroxystyrene (Tg 174° C.), ring-amino-substituted vinyl aromatics including 4-amino styrene, ring-silyl-substituted styrenes such as p-dimethylethoxy siloxy styrene, unsubstituted and substituted vinyl pyridines such as 2-vinyl pyridine (Tg 104° C.) and 4-vinyl pyridine (Tg 142° C.), and other vinyl aromatic monomers such as vinyl carbazole (Tg 227° C.) and vinyl ferrocene (Tg 189° C.); (2) other vinyl monomers including (a) vinyl esters such as vinyl benzoate (Tg 71° C.), vinyl 4-tert-butyl benzoate (Tg 101° C.), vinyl cyclohexanoate (Tg 76° C.), vinyl pivalate (Tg 86° C.), vinyl trifluoroacetate (Tg 46° C.), vinyl butyral (Tg 49° C.), (b) vinyl amines, (c) vinyl halides such as vinyl chloride (Tg 81° C.) and vinyl fluoride (Tg 40° C.), (d) alkyl vinyl ethers such as tert-butyl vinyl ether (Tg 88° C.) and cyclohexyl vinyl ether (Tg 81° C.), and (e) other vinyl compounds such as vinyl pyrrolidone; (3) other aromatic monomers including acenaphthalene (Tg 214° C.) and indene (Tg 85° C.); (4) methacrylic monomers including (a) methacrylic acid anhydride (Tg 159° C.), (b) methacrylic acid esters (methacrylates) including (i) alkyl methacrylates such as methyl methacrylate (Tg 105-120° C.), ethyl methacrylate (Tg 65° C.), isopropyl methacrylate (Tg 81° C.), isobutyl methacrylate (Tg 53° C.), t-butyl methacrylate (Tg 118° C.) and cyclohexyl methacrylate (Tg 92° C.), (ii) aromatic methacrylates such as phenyl methacrylate (Tg 110° C.) and including aromatic alkyl methacrylates such as benzyl methacrylate (Tg 54° C.), (iii) hydroxyalkyl methacrylates such as 2-hydroxyethyl methacrylate (Tg 57° C.) and 2-hydroxypropyl methacrylate (Tg 76° C.), (iv) additional methacrylates including isobornyl methacrylate (Tg 110° C.) and trimethylsilyl methacrylate (Tg 68° C.), and (c) other methacrylic-acid derivatives including methacrylonitrile (Tg 120° C.); (5) acrylic monomers including (a) certain acrylic acid esters such as tert-butyl acrylate (Tg 43-107° C.), hexyl acrylate (Tg 57° C.) and isobornyl acrylate (Tg 94° C.); and (b) other acrylic-acid derivatives including acrylonitrile (Tg 125° C.).

As used herein, a poly(vinyl aromatic) block is a polymer block that contains multiple copies of one or more types of vinyl aromatic monomers, a polyalkene block is a block that contains multiple copies of one or more types of alkene monomers, a polyacrylic block is a block that contains multiple copies of one or more types of acrylic monomers, a polymethacrylic block is a block that contains multiple copies of one or more types of methacrylic monomers, a polysiloxane block is a block that contains multiple copies of one or more types of siloxane monomers, and so forth.

As will be appreciated by those of ordinary skill in the art, polymer blocks such as those above may be synthesized according to known methods, including cationic, anionic, and radical polymerization methods, particularly controlled/"living" cationic, anionic and radical polymerizations.

Many of the above polymer blocks may be formed using free radical polymerization processes such as metal-catalyzed atom transfer radical polymerization (ATRP), stable free-radical polymerization (SFRP), including nitroxide-mediated processes (NMP), degenerative transfer including reversible addition-fragmentation chain transfer (RAFT) processes, or other controlled radical polymerization processes. These methods are well-detailed in the literature and are described, for example, in an article by Pyun and Matyjaszewski, "Synthesis of Nanocomposite Organic/Inorganic Hybrid Materials Using Controlled/"Living" Radical Polymerization," Chem. Mater., 13:3436-3448 (2001); B. Reeves, "Recent Advances in Living Free Radical Polymerization," Nov. 20, 2001, University of Florida; and T. Kowalewski et al., "Complex nanostructured materials from segmented copolymers prepared by ATRP," Eur. Phys. J. E, 10, 5-16 (2003).

ATRP is an appealing free radical polymerization technique, as it is tolerant of a variety of functional groups (e.g., alcohol, amine, and sulfonate groups, among others) and thus allows for the polymerization of many monomers. In monomer polymerization via ATRP, radicals are commonly generated using organic halide initiators and transition-metal complexes. Some typical examples of organic halide initiators include alkyl halides, haloesters (e.g., methyl 2-bromopropionate, ethyl 2-bromoisobutyrate, etc.) and benzyl halides (e.g., 1-phenylethyl bromide, benzyl bromide, etc.). A wide range of transition-metal complexes may be employed, including a variety of Ru-, Cu-, Os- and Fe-based systems. Examples of monomers that may be used in ATRP polymerization reactions include various unsaturated monomers such as alkyl methacrylates, alkyl acrylates, hydroxyalkyl methacrylates, vinyl esters, vinyl aromatic monomers, acrylamides, methacrylamides, acrylonitrile, and 4-vinylpyridine, among others. In ATRP, at the end of the polymerization, the polymer chains are capped with a halogen atom that can be readily transformed via $S_N1$, $S_N2$ or radical chemistry to provide other functional groups such as amino groups, among many others. Functionality can also be introduced into the polymer by other methods, for example, by employing initiators that contain functional groups which do not participate in the radical polymerization process. Examples include initiators with epoxide, azido, amino, hydroxyl, cyano, and allyl groups, among others. In addition, functional groups may be present on the monomers themselves.

Where all monomers in a given block copolymer are polymerizable by the same technique (e.g., ATRP), such polymers may be formed, for example, by sequential monomer addition.

Various strategies are also available for forming block copolymers from monomers which are polymerizable by differing techniques. For example, such polymers may be formed by the following techniques, among others: (a) one or more end groups of a preexisting polymer may be used (or converted such that they may be used) as initiators in a subsequent polymerization step (i.e., as a so-called "macroinitiator"), (b) one or more side groups of a preexisting polymer may be used (or converted such that they may be used) as initiators in a subsequent polymerization step, (c) a polymerizable group (e.g., a vinyl group, cyclic ether, cyclic ester, etc. group) may be attached to the end of a preexisting polymer, which may subsequently be used in a homopolymerization or copolymerization reaction step (i.e., as a so-called "macromonomer"), and (d) two or more differing polymers may be attached to one another using suitable coupling chemistry, among other schemes. One example of a coupling technique is step growth click coupling, which can be used in conjunction with atom transfer radical polymerization. See, e.g., N. V. Tsarevsky et al. Macromolecules, 2005, 38, 3558).

For example, block copolymers comprising a peptide or peptoid block and a free radical polymerized block can be formed using various known techniques, many of which are discussed in the Ayres reference cited above. A few examples include the following: (1) Polymers may be synthesized from the end group(s) of a peptide or peptoid using the peptide or peptoid as a free radical initiator. For example, peptides have been functionalized to form an NMP initiator while on the resin (from which t-butyl acrylate has been polymerized, followed by styrene polymerization), peptides have been functionalized to form an ATRP initiator while on the resin (from which 2-hydroxyethyl methacrylate has been polymerized), peptides have been functionalized to from an ATRP initiator after detachment from the resin (e.g., by functionalization with 2-bromo-isobutyric acid, from which monomers such as n-butyl acrylate and methyl methacrylate have been polymerized by ATRP), and peptides have been functionalized to form an ATRP initiator after detachment, which was then switched to a RAFT initiator (and from which n-butyl acrylate was polymerized). (2) Polymers may be synthesized from the side group(s) of peptides or peptoids using the peptide or peptoid as an initiator. For example, alcohol groups of serine peptides have been functionalized with an alpha-bromo ester and the resulting entity used for the ATRP of methyl methacrylate, (3) Monomers may be formed from peptides or peptoids (e.g., by attaching a vinyl group) and subsequently used in free radical polymerization reactions. For example, a methacrylamide functionalized peptide has been reacted with N-(2-hydroxypropyl)-methacrylamide via free radical polymerization, peptide monomers have been formed by reacting the terminal —COOH group of the peptide with hydroxyethyl methacrylate, followed by polymerization by ATRP using a bifunctional initiator, followed in turn by ATRP with methyl methacrylate to form a triblock copolymer, peptide monomers formed using 2-isocyanatoethyl methacrylate have been polymerized by ATRP using a bifunctional PEG-based initiator, which was functionalized with 2-bromo-isobutyric acid, to form a triblock copolymer, and norbonene functionalized peptides have been homo- and co-polymerized via ROMP. (4) Preformed polymers may be coupled to the terminal groups of pre-formed peptides (e.g., to primary amino groups) using standard peptide chemistry, or they may be coupled to side groups of preformed peptides (e.g., to cystiene groups), which reactions are also applicable to peptoids. (5) Preformed peptides or peptoids may be coupled to side groups of preformed polymers (e.g., an acrylate having activated ester groups, polymerized by RAFT).

As noted above, polymeric devices in accordance with the present invention may optionally contain at least one therapeutic agent. "Therapeutic agents," "drugs," "pharmaceutically active agents," "pharmaceutically active materials," and other related terms may be used interchangeably herein. A wide variety of therapeutic agents can be employed in conjunction with the present invention including those used for the treatment of a variety of diseases and conditions (i.e., the prevention of a disease or condition, the reduction or elimination of symptoms associated with a disease or condition, or the substantial or complete elimination of a disease or condition). Numerous therapeutic agents are described below.

The rate of release of therapeutic agents from a polymeric layer in accordance with the invention with depend, for example, on the nature of the therapeutic agents within the layer, the nature of the block copolymers within the layer (e.g., molecular weight, architecture, and monomer composition), and the nature any other optional supplemental species, including supplemental polymers, within the layer. For instance, the nature of the therapeutic agents (e.g., hydrophilic/hydrophobic) and the nature of the polymer blocks (e.g., hydrophilic/hydrophobic/swellable) within the block copolymer(s) will have a significant effect upon the release of the drug (affecting, for example, the wettability of the polymeric regions, the water diffusivity, the therapeutic agent diffusivity, and so forth). The nature of the polymeric layer may also be modified by optionally adding supplemental hydrophobic and/or hydrophilic polymers to the layer.

Exemplary therapeutic agents for use in conjunction with the present invention include the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD or YIGSR peptide-containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine) (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin(sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives and tranilast, (bb) endothelialization facilitators such as VEGF and RGD and YIGSR peptides, and (cc) blood rheology modulators such as pentoxifylline.

Several preferred therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

A wide range of therapeutic agent loadings may be used in conjunction with the medical devices of the present invention. Typical loadings range, for example, from than 1 wt % or less to 2 wt % to 5 wt % to 10 wt % to 25 wt % or more of the polymeric region.

As previously indicated, in one aspect, the invention provides medical devices that include (a) a substrate and (b) a coating that includes an antifouling copolymer, an adhesive copolymer, or both. The antifouling copolymer contains at least one antifouling polymer block and at least one additional polymer block. Similarly, the adhesive copolymer contains at least one adhesive polymer block and at least one additional polymer block.

Several specific examples of this aspect of the invention will now be discussed with reference to the drawings.

FIG. 1 is a schematic, cross-sectional view of a portion of a medical device 100, in accordance with an embodiment of the present invention. The medical device 100 shown includes a substrate portion 110, whose surface may comprise, for example, a metal oxide species. For example, the substrate may be formed from (a) a metal oxide such as aluminum or zirconium oxide, among others or (b) a metal with a native oxide surface such as stainless steel, nitinol, or titanium, among others. Over the substrate is provided a coating 120, which includes a first coating layer 120a that comprises an adhesive copolymer disposed over and in contact with the substrate 110, and a second coating layer 120b that comprises a polymer that is compatible with the adhesive copolymer, which is disposed over and in contact with the first coating layer 120a. The adhesive copolymer in the first layer 120a may comprise, for example, at least one adhesive polymer block having multiple ring-hydroxyl-substituted aromatic groups along its backbone, which groups are known to provide good adhesion to metal oxides, and at least one additional block. A therapeutic agent may optionally be provided in the coating 120, for example, disposed within the first layer 120a, the second layer 120b, or both.

The polymer in the second layer 102b may be, for example, an antifouling copolymer which comprises at least one antifouling polymer block having multiple alkoxy functional groups along its backbone, which are known to reduce protein fouling, and at least one additional polymer block. At least one additional block of the antifouling copolymer is compatible with the at least one additional block of the adhesive copolymer, thereby promoting adhesion between the first layer 120a and the second layer 120b. For example, at least one additional polymer block of the antifouling copolymer may be at least partially miscible with at least one additional polymer block of the adhesive copolymer. Compatibility may be achieved, for example, by making the monomer content of at least one additional block of the antifouling copolymer the same as the monomer content of at least one additional block of the adhesive copolymer.

In another example, the second layer 120b may comprise a biocompatible block copolymer which has at least one block that is compatible with at least one block of the adhesive copolymer. For example, at least one block of the biocompatible polymer may be at least partially miscible with at least one block of the adhesive copolymer. As above, compatibility may be achieved, for example, by selecting polymer blocks that are different from one another in monomer content yet are miscible with one another, or by making the monomer content of at least one block of the biocompatible copolymer the same as the monomer content of at least one additional block of the adhesive copolymer.

Figure 2:
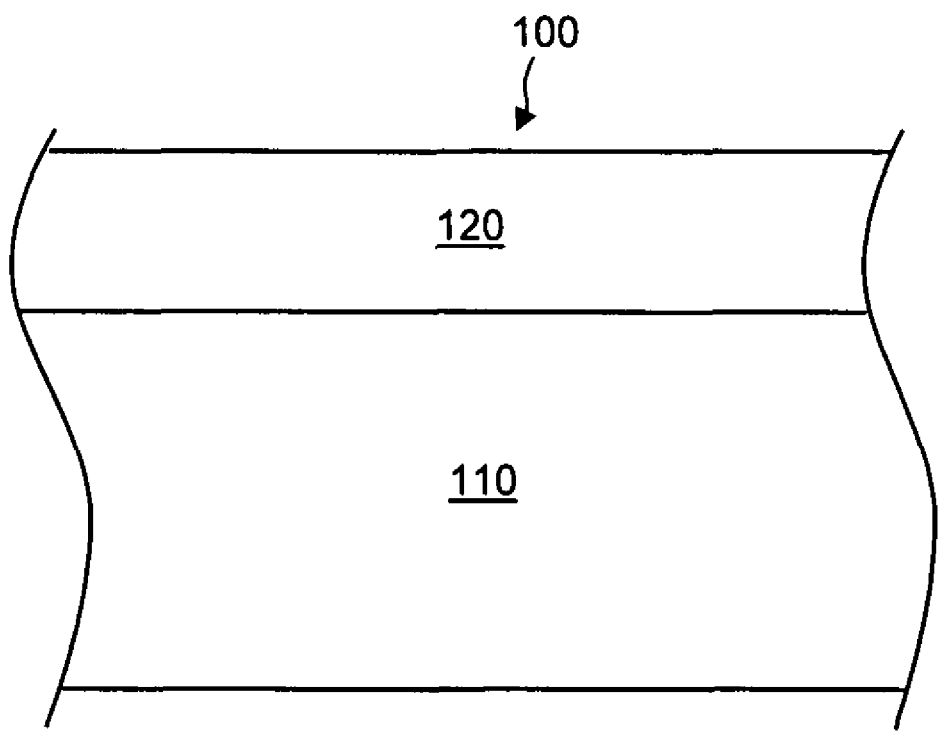
FIG. 2 is a schematic, partial cross-sectional view of a medical device, in accordance with another aspect of the invention.

FIG. 2 is a schematic, cross-sectional view of a portion of medical device 100 in accordance with another embodiment of the present invention. The medical device shown includes a substrate portion 110 and a single-layer coating 120.

In one embodiment, the coating 120 may comprise, for example, an antifouling copolymer, an adhesive copolymer and an optional therapeutic agent. The adhesive copolymer may comprise, for example, at least one adhesive polymer block having multiple ring-hydroxyl-substituted aromatic groups along its backbone, thereby providing good adhesion between the coating 120 and the underlying substrate 110.

The antifouling copolymer may comprise, for example, at least one antifouling polymer block having multiple alkoxy functional groups along its backbone, thereby reducing protein fouling. Moreover, by ensuring that at least one additional block of the antifouling copolymer is compatible with at least one additional block of the adhesive copolymer, mechanical integrity of the coating 120 may be enhanced.

In another embodiment, the coating 120 may comprise an antifouling copolymer while not comprising an adhesive polymer as described above. In this embodiment, the antifouling copolymer may comprise at least one antifouling polymer block having multiple alkoxy functional groups along its backbone, which are known to reduce protein fouling, and at least one additional polymer block, for instance, a biodegradable polymer block (e.g., a biodegradable homopolymer and copolymer block such as a polyester block, poly(ortho ester) block, polyanhydride block, tyrosine-based polymer block, etc.) or a biostable poly(unsaturated monomer) block such as an polyalkene block (e.g., formed from ethylene, n- or iso-propylene, n-, sec-, iso- or tert-butylene, etc.), a polyacrylate block (e.g., formed from methyl acrylate, ethyl acrylate, n- or iso-propyl acrylate, n-, sec-, iso- or tert-butyl acrylate, etc.), a polymethcrylate block (e.g., formed from methyl methacrylate, ethyl methacrylate, n- or iso-propyl methacrylate, n-, sec-, iso- or tert-butyl methacrylate, etc.), a polyvinyl aromatic block (e.g., styrene, α-methyl styrene, etc.), and so forth.

In another embodiment, the coating 120 may comprise an adhesive copolymer while not comprising an antifouling polymer like that described above. In this embodiment, the adhesive copolymer may comprise at least one adhesive polymer block having multiple ring-hydroxyl-substituted aromatic functional groups along its backbone and at least one additional polymer block, for instance, a biodegradable polymer block or a biostable poly(unsaturated monomer) block, such as those described above, among others.

In yet another embodiment, the coating 120 may comprise a copolymer that comprises least one adhesive polymer block having multiple ring-hydroxyl-substituted aromatic groups along its backbone, at least one antifouling polymer block having multiple alkoxy functional groups along its backbone, and at least one additional polymer block, for example, a biodegradable block or a poly(unsaturated monomer) block, such as those described above, among others.

Numerous techniques are available for forming layers in accordance with the present invention.

For example, where a layer is formed from one or more polymers having thermoplastic characteristics, a variety of standard thermoplastic processing techniques may be used. Using these techniques, a layer can be formed, for instance, by (a) first providing a melt that contains polymer(s) as well as any other optional agents such as therapeutic agent(s) and any supplemental agents and (b) subsequently cooling the melt.

Other processing techniques besides thermoplastic processing techniques may also be used to form layers, including solvent-based techniques. Using these techniques, a polymeric layer can be formed, for instance, by (a) first providing a solution or dispersion that contains polymer(s) as well as any other desired optional agents such as therapeutic agent(s) and any supplemental agents and (b) subsequently removing the solvent. The solvent that is ultimately selected will contain one or more solvent species, which are generally selected based on their ability to dissolve or disperse the various species making up the layer (e.g., polymers, optional agents, etc.), in addition to other factors, including drying rate, surface tension, etc.

Preferred thermoplastic and solvent-based techniques include, for example, spraying techniques, dipping techniques, spin coating techniques, web coating techniques, techniques involving coating via mechanical suspension including air suspension, ink jet techniques, electrostatic techniques, and combinations of these processes.

EXAMPLES

The following examples utilize a peptide mimetic polymer (PMP) of the formula to follow, or portions thereof:

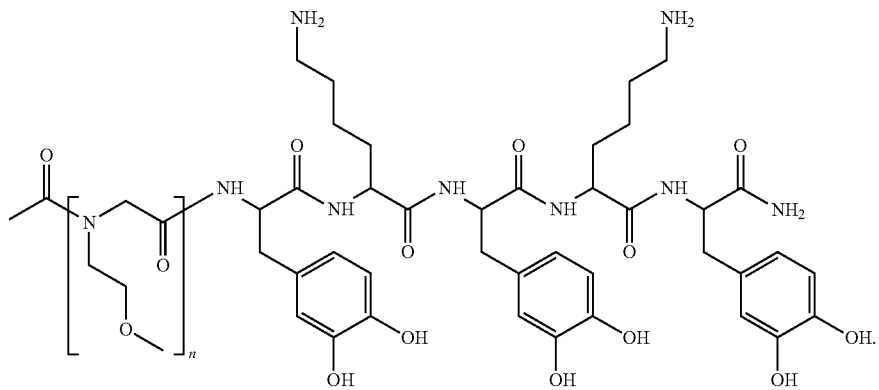

PMP has been shown to strongly adhere to metallic surfaces and to possess very good long term antifouling characteristics. See, e.g., A. R. Statz et al. *J. Am. Chem. Soc.* 2005, 127, 7972-7973). Surface adhesion of PMP to metallic surfaces is obtained from the amino acid polymer bock. Good adhesion is believed to be achieved through metal oxide charge-transfer complexation by the 3,4-dihydroxyphenylalanine (DOPA) residues. The lysine residues are also believed to play an important role in the strength of adhesion, and it has been postulated that the cationic lysine residues may contribute to long-range electrostatic interactions to supplement the DOPA-mediated surface binding. Long term antifouling is believed to be obtained from the N-substituted glycine polymer block, where n is typically about 20. PMP has been shown to exhibit long term resistance to fibroblast cell attachment in excess of 5 months under biweekly cell seeding.

Example 1

A medical device is coated with two layers. The first is a layer of PMP which acts as an adhesive copolymer having a polyamino acid adhesive block and an additional peptoid block of poly(N-substituted glycine). As a variation, an additional polymer block may be inserted into the PMP to space the polyamino acid adhesive block from the peptoid block. For example, Fmoc, submonomer and ATRP synthesis techniques, among others, may be utilized to create well defined block copolymers with a wide range of architectures as described above. The first layer is applied to a metallic surface, for example, a titanium or stainless steel surface, by any suitable method known in the art, for instance, dip, spray or spin coating. This layer adheres to metallic surface through the polyamino acid block of the adhesive copolymer as described above.

The second layer is formed from an antifouling copolymer which contains at least one poly(N-substituted glycine) antifouling block, for example, matching that found in the underlying PMP, and at least one additional block, for example, a hydrophobic poly(unsubstituted monomer) block such as a polystyrene block. For example, the antifouling copolymer may be a diblock or triblock copolymer, among other possibilities. In addition to providing antifouling character, the N-substituted glycine block of the antifouling copolymer promotes adhesion of with the underlying first layer, for example, due to its compatibility with the surface adhered N-substituted glycine chains of the PMP in the first layer, which compatibility may, for example, lead to inter-diffusion and/or other interaction between the N-substituted glycine blocks. The second layer may be applied to the first layer by any suitable method known in the art such as those set forth above.

An advantage of the second layer is that the weight ratio of the polymer blocks to one another, for example, the ratio of the polystyrene blocks to the N-substituted glycine blocks, may be adjusted to produce the desired combination of mechanical properties and protein resistance. Moreover, in the event that the upper layer comprises one or more therapeutic agents, for example, an antithrombotic agent and/or an antiproliferative agent, the ratio may be adjusted to produce a desired release profile. The mechanical, antifouling and drug release characteristics may also be adjusted by varying the architecture of the antifouling copolymer (e.g., linear, star, comb, dendritic, etc.).

Example 2

A medical device is coated with two layers. The first layer contains an adhesive copolymer which incorporates poly(3,4-dihydroxyphenylalanine) or poly(3,4-dihydroxyphenylalanine-co-lysine) as an adhesive block and an additional polymer block, for example, a hydrophobic poly(unsaturated monomer) block such as a polystyrene block. The second layer contains an antifouling copolymer like that used in Example 1. As in Example 1, one or more therapeutic agents may optionally be loaded into the coating, and the first and second layers can be applied to the medical device substrate using standard coating processes known in the art. Adhesion between the layers is promoted by the mutual compatibility of the polystyrene blocks in the adhesive and antifouling copolymers in the first and second layers, respectively, which compatibility may, for example, lead to inter-diffusion and/or other interaction between the polystyrene blocks.

Example 3

A medical device is coated with two polymeric layers using standard coating processes known in the art. The first polymeric layer comprises poly(3,4-dihydroxyphenylalanine) or poly(3,4-dihydroxyphenylalanine-co-lysine), which imparts adhesive character to the layer. For example, an adhesive copolymer having a poly(3,4-dihydroxyphenylalanine-alt-lysine) block and a hydrophobic poly(unsaturated monomer) block, for instance, a high Tg block such as a polystyrene block or a low Tg block such as a polyisobutylene block may be prepared.

A second polymeric layer containing a block copolymer in which two or more high Tg blocks are separated by a low Tg block is formed over the first layer. For instance, the second layer may contain a poly(styrene-b-isobutylene-b-styrene), which may be formed as described in U.S. Pat. No. 6,545,097 to Pinchuk et al. Polymers of this type are capable of demonstrating high strength and elastomeric properties, while at the same time being processable using techniques such as solvent- and/or melt-based processing techniques. As is well known, block copolymers tend to phase separate. In the polymers like those described above, the high Tg blocks (which are hard) will aggregate to form hard phase domains. Without wishing to be bound by theory, because the high Tg hard blocks are interconnected via low Tg blocks, the hard phase domains become physically crosslinked to one another via the elastomeric blocks. Moreover, because the crosslinks are not covalent in nature, they can be reversed, for example, by dissolving or melting the block copolymer.

As above, one or more therapeutic agents may optionally be loaded into the coating, and the first and second layers can be applied to the medical device substrate using standard coating processes known in the art.

Example 4

A medical device is coated with a single polymeric layer using standard coating processes known in the art. This polymeric layer comprises poly(N-substituted glycine) blocks, which impart antifouling functionality to the polymer layer and to the outer exposed surface of the device. For example, an antifouling copolymer having a poly(N-substituted glycine) block and a hydrophobic poly(unsaturated monomer) block such as a polystyrene block may be prepared. One or more optional therapeutic agents may be loaded into the coating. As above, various polymer block ratios and polymer architectures may be used to adjust the mechanical and protein resistant characteristics of the layer, as well as the release characteristics of the layer in the event that one or more therapeutic agents are included.

Example 5

A medical device is coated with a single polymeric layer using standard coating processes known in the art. This polymeric layer comprises a copolymer having peptoid block to impart adhesive character to the layer a peptide block to impart antifouling character. The copolymer further comprises a biodegradable block. For example, the copolymer may contain (a) a poly(3,4-dihydroxyphenylalanine) or poly (3,4-dihydroxyphenylalanine-co-lysine) block, (b) a poly(N-substituted glycine) block or (c) a polylactide, polylactide-co-glycolide, polycaprolactone, or tyrosine based polymer block. Fmoc, submonomer and ring opening polymerization synthesis techniques, among others, may be utilized to create well defined block copolymers with a wide range of architectures. As above, one or more therapeutic agents may optionally be loaded into the polymeric layer.

Example 6

A medical device is coated with a two polymeric layers using standard coating processes known in the art. The first polymeric layer comprises an adhesive copolymer having a peptoid block to impart adhesive character to the layer and a biodegradable/bioabsorbable block. The second layer comprises an antifouling copolymer having a peptide block to impart antifouling character and a biodegradable/bioabsorbable block which matches that of the adhesive copolymer. As above, one or more therapeutic agents may optionally be loaded into the polymeric layer.

Example 7

A medical device is coated with a two polymeric layers using standard coating processes known in the art. The first polymeric layer comprises PMP which imparts adhesive character to the layer. The second layer comprises a biodegradable/bioabsorbable block and a poly(N-substituted glycine block) like that of the PMP, to provide adhesion to the underlying layer and to promote antifouling character to the outer layer surface. As above, one or more therapeutic agents may optionally be loaded into the polymeric layer.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising: (1) a substrate; and (2) a first layer that comprises (a) an antifouling copolymer which comprises (i) an antifouling polymer block that comprises multiple pendant alkoxy functional groups and (ii) a first additional polymer block that is different from the antifouling polymer block and is selected from a biostable polymer block, a biodegradable polyester block, a biodegradable poly(ortho ester) block, a biodegradable polyanhydride block and a biodegradable tyrosine-based polymer block and (b) an adhesive copolymer which comprises (i) an adhesive polymer block and (ii) a second additional polymer block that is different from the adhesive polymer block and has a monomer content that is the same as that of the first additional polymer block, wherein said antifouling copolymer and said adhesive copolymer are different.

2. The medical device of claim 1, wherein the first additional polymer block is a biostable poly(unsaturated monomer) block.

3. The medical device of claim 1, wherein the first additional polymer block is a biostable high Tg poly(unsaturated monomer) block.

4. The medical device of claim 1, wherein the first additional polymer block is a biostable low Tg poly(unsaturated monomer) block.

5. The medical device of claim 1, wherein the first additional polymer block is a biodegradable polyester block.

6. The medical device of claim 1, wherein the first additional polymer block is a biodegradable tyrosine-based polymer block.

7. The medical device of claim 2, wherein the poly(unsaturated monomer) block comprises vinyl aromatic monomers, acrylic monomers, methacrylic monomers, alkene monomers, or a combination thereof.

8. The medical device of claim 1, wherein the first layer further comprises a therapeutic agent.

9. The medical device of claim 1, wherein the alkoxy groups are $C_1$-$C_5$-alkoxy groups.

10. The medical device of claim 1, wherein the alkoxy groups are alkoxyalkyl groups.

11. The medical device of claim 10, wherein the alkoxyalkyl groups are $C_1$-$C_5$-alkoxy-$C_1$-$C_5$-alkyl groups.

12. The medical device of claim 10, wherein the alkoxyalkyl groups are methoxyethyl groups.

13. The medical device of claim 1, wherein the antifouling polymer block comprises a polyamide polymer backbone.

14. The medical device of claim 1, wherein the antifouling polymer block comprises a peptoid.

15. The medical device of claim 14, wherein the peptoid comprises a poly(N-alkoxyalkyl glycine) chain.

16. The medical device of claim 14, wherein the peptoid comprises a poly(N-methoxyethyl glycine) chain.

17. The medical device of claim 14, wherein the peptoid comprises a polymer chain of the formula

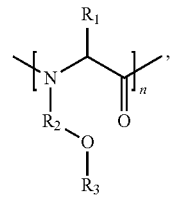

where n is an integer of 3 or more, $R_1$ and $R_2$ are independently selected from H, $C_1$-$C_6$ alkyl, $C_1$-$C_6$ alkene, aromatic, $C_1$-$C_6$ alkyl in combination with N, O, or S, $C_1$-$C_6$ alkene in combination with N, O, or S, and $C_6$-$C_{10}$ aromatic in combination with N, O, or S, and wherein $R_3$ is $C_1$-$C_6$ alkyl.

18. The medical device of claim 1, wherein the antifouling polymer comprises a poly(N-methoxyethyl glycine) block and a biostable poly(unsaturated monomer) block.

19. The medical device of claim 1, wherein the adhesive polymer block comprises multiple pendant ring-hydroxyl-substituted aromatic groups.

20. The medical device of claim 19, wherein said ring-hydroxyl-substituted aromatic groups comprise ring-hydroxyl-substituted $C_6$-$C_{12}$-aromatic groups.

21. The medical device of claim 19, wherein said ring-hydroxyl-substituted aromatic groups comprise dihydroxyphenyl groups.

22. The medical device of claim 19, wherein said ring-hydroxyl-substituted aromatic groups comprise 3,4-dihydroxyphenyl groups.

23. The medical device of claim 19, wherein said ring-hydroxyl-substituted aromatic groups comprise 3,4-dihydroxyphenylalkyl groups.

24. The medical device of claim 19, wherein said ring-hydroxyl-substituted aromatic groups comprise 3,4-dihydroxyphenylalkyl groups.

25. The medical device of claim 19, wherein said adhesive polymer block further comprises multiple amino-alkyl groups along the polymer backbone.

26. The medical device of claim 19, wherein said adhesive polymer block further comprises multiple amino-$C_1$-$C_{10}$-alkyl groups along the polymer backbone.

27. The medical device of claim 19, wherein said adhesive polymer block further comprises multiple amino-$C_2$-$C_6$-alkyl groups along the polymer backbone.

28. The medical device of claim 19, wherein said adhesive polymer block comprises a polyamide backbone.

29. The medical device of claim 19, wherein said adhesive polymer block comprises a poly(amino acid) chain.

30. The medical device of claim 29, wherein said poly(amino acid) chain comprises multiple 3,4 dihydroxyphenyl alanine units.

31. The medical device of claim 29, wherein said poly (amino acid) chain comprises multiple lysine units adjacent multiple 3,4 dihydroxyphenyl alanine units.

32. The medical device of claim 19, wherein the adhesive polymer comprises a poly(3,4 dihydroxyphenyl alanine-alt-lysine) block and a poly(unsaturated monomer) block.

33. A medical device comprising: (a) a substrate; (b) a first layer that comprises an antifouling copolymer which comprises (i) an antifouling polymer block that comprises multiple pendant alkoxy functional groups and (ii) a first additional polymer block that is different from the antifouling polymer block and is selected from a biostable polymer block, a biodegradable polyester block, a biodegradable poly(ortho ester) block, a biodegradable polyanhydride block and a biodegradable tyrosine-based polymer block; and (c) a second layer in addition to said first layer, wherein the second layer is disposed between the first layer and the substrate, wherein the second layer is in contact with the first layer and the substrate, and wherein the second layer comprises an adhesive copolymer that comprises (i) an adhesive polymer block and (ii) a second additional polymer block that is different from the adhesive polymer block and has a monomer content that is the same as that of the first additional polymer block, wherein said antifouling copolymer and said adhesive copolymer are different, and wherein said first and second layers are different.

34. The medical device of claim 33, wherein the adhesive polymer block comprises multiple pendant ring-hydroxyl-substituted aromatic groups.

35. A medical device comprising: (a) a substrate; (b) a first layer disposed on said substrate, said first layer comprising an adhesive copolymer comprising (i) an adhesive polymer block that comprises multiple pendant ring-hydroxyl-substituted aromatic groups and (ii) a first additional polymer block that is different from the adhesive polymer block; and (c) a second layer disposed on said first layer, said second layer comprising a block copolymer comprising first and second polymer blocks that differ from one another, wherein one of the first and second polymer blocks of the block copolymer has the same monomer content as the first additional polymer block of the adhesive copolymer, wherein said adhesive copolymer and said block copolymer are different, and wherein said first and second layers are different.

36. The medical device of claim 35, wherein the first polymer block is a high Tg polymer block and the second polymer block is a low Tg polymer block.

37. The medical device of claim 35, wherein the first polymer block is an antifouling polymer block that comprises multiple pendant alkoxy functional groups and the second polymer block is a biostable polymer block.

38. The medical device of claim 35, wherein the first polymer block is an antifouling polymer block that comprises multiple alkoxy functional groups along its backbone and the second polymer block is a biodegradable polymer block.

39. The medical device of claim 35, wherein the second layer further comprises a therapeutic agent.

40. The medical device of claim 19, wherein the first additional polymer block is a biodegradable polyester block.

41. The medical device of claim 33, wherein the first additional polymer block is a biodegradable polyester block.

42. The medical device of claim 34, wherein the first additional polymer block is a biodegradable polyester block.

* * * * *